United States Patent
Mattila et al.

(10) Patent No.: US 7,662,339 B2
(45) Date of Patent: Feb. 16, 2010

(54) APPARATUS HAVING IMPROVED GANTRY ASSEMBLY SUITABLE FOR USE IN A LABORATORY ENVIRONMENT

(75) Inventors: Robert J. Mattila, Prior Lake, MN (US); Brian D. Wilson, Chaska, MN (US)

(73) Assignee: Beckman Coulter, Inc., Fullerton, CA (US)

( * ) Notice: Subject to any disclaimer, the term of this patent is extended or adjusted under 35 U.S.C. 154(b) by 858 days.

(21) Appl. No.: 10/972,164

(22) Filed: Oct. 22, 2004

(65) Prior Publication Data

US 2006/0088443 A1 Apr. 27, 2006

(51) Int. Cl.
B01L 3/02 (2006.01)
(52) U.S. Cl. ............................. 422/67; 422/63; 422/65; 422/100
(58) Field of Classification Search .................. 422/63, 422/65, 67, 100
See application file for complete search history.

(56) References Cited

U.S. PATENT DOCUMENTS

| | | | |
|---|---|---|---|
| 3,178,266 A * | 4/1965 | Anthon | 422/64 |
| 4,271,699 A | 6/1981 | Williamson | |
| 4,501,164 A | 2/1985 | Stockdale et al. | |
| 4,802,377 A | 2/1989 | Keppler | |
| 4,803,050 A * | 2/1989 | Mack | 422/65 |
| 4,875,228 A | 10/1989 | Archer | |
| 5,181,599 A | 1/1993 | Blatt | |
| 5,215,181 A | 6/1993 | Blatt | |
| 5,296,195 A | 3/1994 | Pang et al. | |
| 5,306,510 A * | 4/1994 | Meltzer | 422/65 |
| 5,653,571 A | 8/1997 | Lizenby | |
| 5,911,631 A * | 6/1999 | Bouldin et al. | 47/1.01 R |
| 6,150,662 A | 11/2000 | Hug et al. | |
| 6,627,156 B1 | 9/2003 | Goodale et al. | |
| 6,776,961 B2 | 8/2004 | Lindsey et al. | |
| 2003/0194349 A1* | 10/2003 | Carey et al. | 422/63 |

* cited by examiner

*Primary Examiner*—Robert J Hill, Jr.
*Assistant Examiner*—Cedric Chan
(74) *Attorney, Agent, or Firm*—Townsend and Townsend and Crew LLP; Charles C. Wong

(57) ABSTRACT

An assembly suitable for use in a laboratory instrument is set forth. The assembly comprises a plurality of guide rods that are disposed generally parallel with one another and a plurality of carriage assemblies connected for movement along the plurality of guide rods. A sub-carriage assembly is disposed on at least one of the carriage assemblies and is connected to the carriage assembly for movement in a direction transverse to the plurality of guide rods. A plurality of carriage drive mechanisms are employed to move the plurality of carriage assemblies independently along said plurality of guide rods and a sub-carriage drive mechanism is provided to move the sub-carriage assembly in a direction transverse to said plurality of guide rods.

19 Claims, 7 Drawing Sheets

APPARATUS HAVING IMPROVED GANTRY ASSEMBLY SUITABLE FOR USE IN A LABORATORY ENVIRONMENT

FIELD OF THE INVENTION

The present invention is generally directed to apparatus used to analyze or otherwise manipulate a chemical and/or biological material. More particularly, the present invention includes an apparatus having an improved gantry assembly on which tools are provided to execute one or more processes in such manipulations wherein the apparatus is suitable for use in a laboratory environment.

BACKGROUND OF THE INVENTION

The manipulation of chemical and/or biological materials in a laboratory environment is often quite labor-intensive. Recent trends in laboratory equipment design therefore point toward greater automation of many of these manipulation steps. Among other things, automation increases the throughput of the analyses executed by the equipment, reduces the costs of manual labor in the laboratory, increases the reliability of the analyses and protects laboratory workers from undesired contact with hazardous chemical and/or biological materials.

One example of an automated assembly suitable for use in a laboratory apparatus is set forth in U.S. Pat. No. 6,627,156, issued Sep. 30, 2003, to Goodale et al. Among other things, the '156 patent discloses a piercing station for piercing container caps or thick stoppers of a container, such as a test tube. The piercing station has a structural frame with two vertical guide rods. A carriage assembly is slidably mounted on the guide rods and is driven to move up and down along them. The carriage assembly carries a blade holder, which, in turn, holds a piercing blade assembly. The blade assembly includes a center blade and to cross blades interlock together, such that the blade assembly has a generally modified H-shaped cross-section for piercing a cap.

In operation, containers having caps that are to be pierced are sequentially shuttled beneath the piercing blade assembly. The piercing blade assembly is then driven through the respective cap to form an opening therein. The pierced container is then shuttled to a further position at which a sampling probe enters the opening and aspirates an amount of the sample material from the interior of the container.

An improvement to the foregoing apparatus to execute closed tube sampling has been implemented in an LxI® Model laboratory instrument manufactured by Beckman Coulter, Inc. In this implementation, the piercing blade and the sampling probe form a single, vertically movable sub-carriage assembly that is fixed to a single, horizontally movable carriage assembly. As a result, the piercing blade and sampling probe both share the same motions. The single carriage assembly is mounted for horizontal movement along a gantry and is driven by a horizontal drive.

In operation, the sample tubes are presented in a rack under the blade/probe hardware. The carriage assembly first translates downward to pierce the closed stopper with the blade. The carriage then retracts upward and shifts horizontally to position the sampling probe above the sample tube. A second downward motion allows the probe to enter the tube through the pierced opening in the cap and to aliquot the sample.

There are several inherent disadvantages when attempting to transfer the specific geometry of the piercing/sampling apparatus to other laboratory apparatus platforms. Many of these disadvantages arise from the fact that various dimensions in the apparatus must be chosen to prevent unwanted interference of the blade and sample probe with the tubes. For example, the motion of the rack must necessarily present the tubes sequentially along a motion path that is perpendicular to the horizontal motion of the single carriage assembly if the size of the rack is to be optimal and accommodate the maximum number of tubes per linear rack length. Further, the spacing between the blade and the probe must be greater than one half of the diameter of the sample tube in order to ensure sequential clearance of the blade and the probe from the sample tube during their respective operations. Such limitations are not inherent in the improved gantry assembly set forth below.

SUMMARY OF THE INVENTION

An assembly suitable for use in a laboratory instrument is set forth. The assembly comprises a plurality of guide rods that are disposed generally parallel with one another and a plurality of carriage assemblies connected for movement along the plurality of guide rods. A sub-carriage assembly is disposed on at least one of the carriage assemblies and is connected to the carriage assembly for movement in a direction transverse to the plurality of guide rods. A plurality of carriage drive mechanisms are employed to move the plurality of carriage assemblies independently along said plurality of guide rods and a sub-carriage drive mechanism is provided to move the sub-carriage assembly in a direction transverse to said plurality of guide rods.

In accordance with various embodiments, each carriage assembly carries a corresponding sub-carriage assembly. Each carriage assembly and corresponding sub-carriage assembly are driven independent of one another. To this end, at least one end of each carriage assembly is connected for movement along at least one of the guide rods and another end of each carriage assembly is connected to another of the guide rods so that rotation of that guide rod results in corresponding transverse motion of the respective sub-carriage assembly.

In accordance with further embodiments of the apparatus, each sub-carriage assembly includes a tool that is used in one or more steps of a processing sequence in which a material in a container is transported, accessed, extracted, manipulated, etc. For example, at least one of the sub-carriage assemblies may include a piercing tool that is adapted to pierce a sealed cap of a container during transverse movement of the corresponding sub-carriage assembly. A further sub-carriage assembly may include a sampling tool that is adapted to enter the container and extract an amount of material from the container during transverse movement thereof through the opening formed by the piercing tool in a prior processing step. In embodiments, one or more of the sub-carriage assemblies may include heads that are adapted to engage a container for transport or other manipulation thereof.

DESCRIPTION OF A PREFERRED EMBODIMENT OF THE INVENTION

Figure 1:
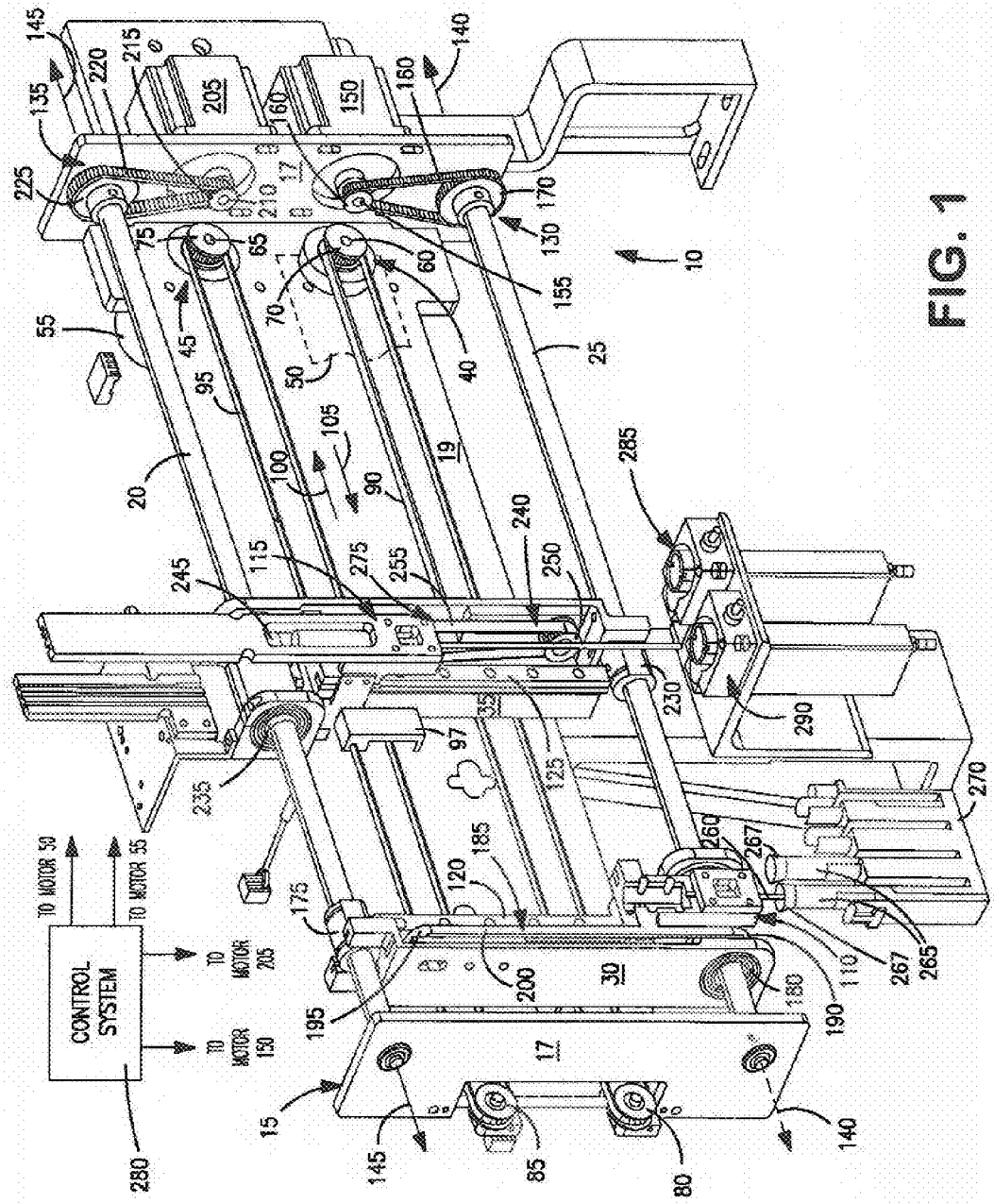
FIG. 1 is a perspective view of one embodiment of a gantry assembly constructed in accordance with the teachings of the present invention in which a blade tool is shown piercing a sealed cap of a container.
Figure 2:
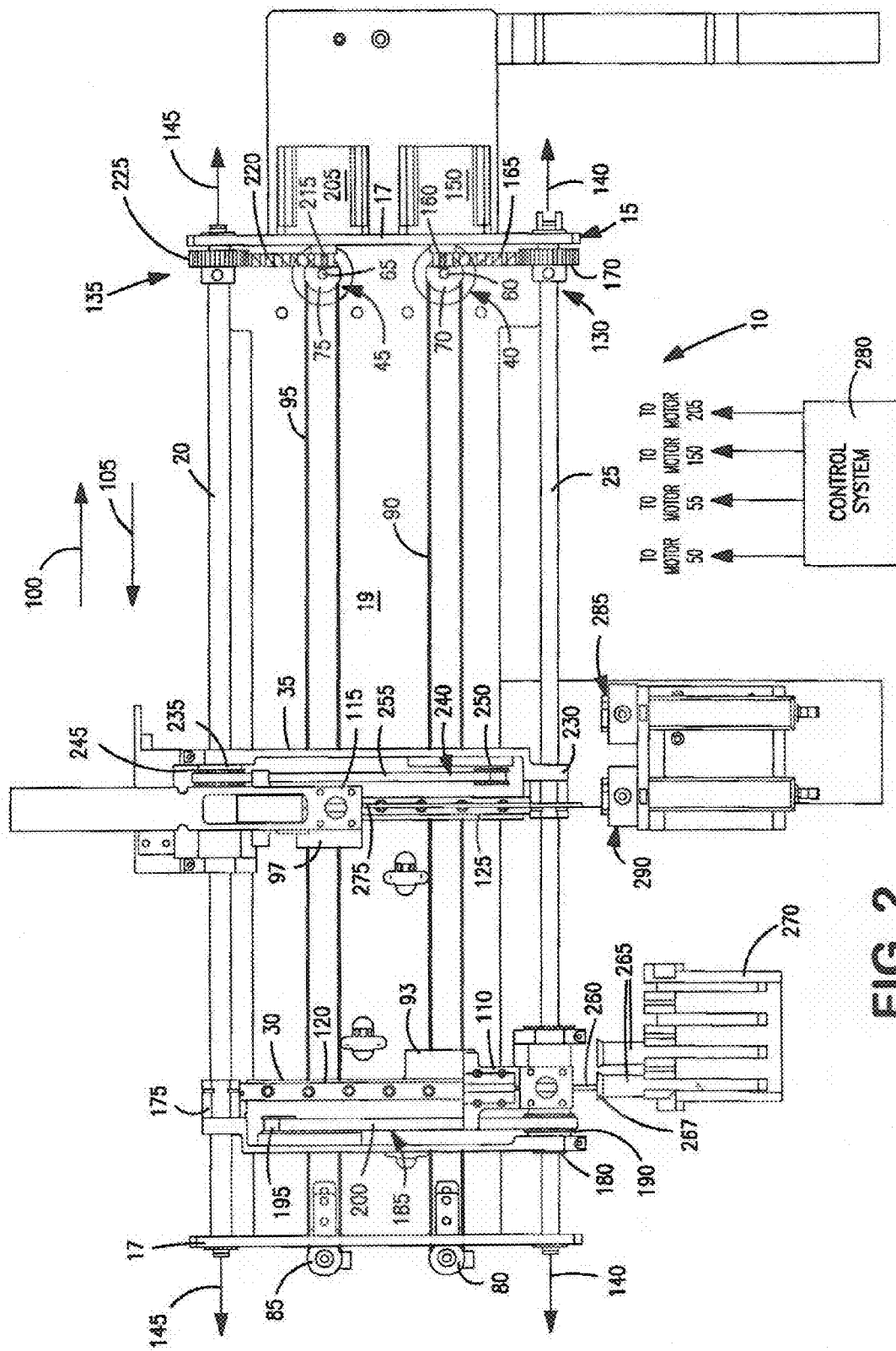
FIG. 2 is a front view of the gantry assembly shown in FIG. 1.
Figure 3:
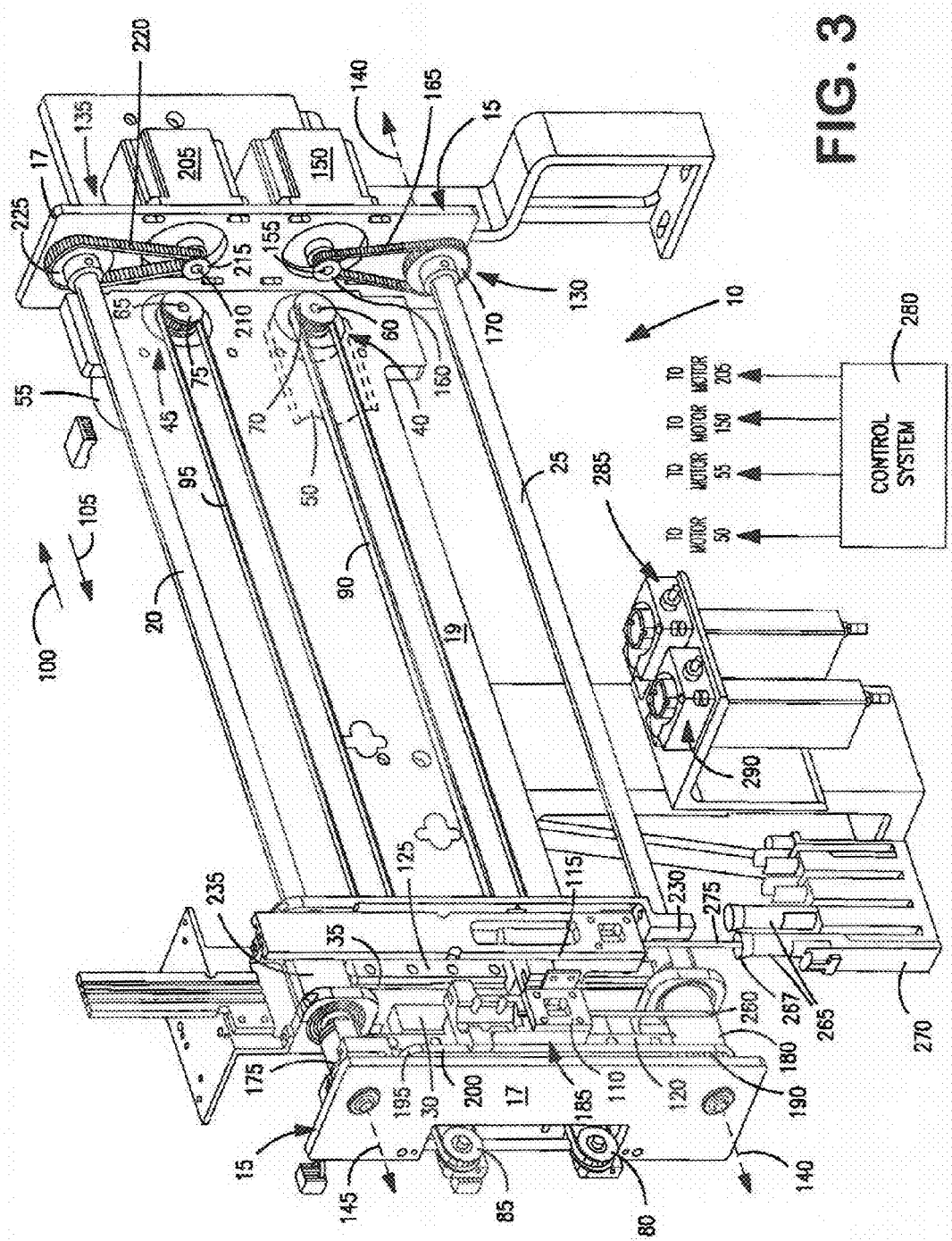
FIG. 3 is a perspective view of the gantry assembly shown in FIG. 1 in which a sampling tool is shown inserted through an opening in the cap of a container.
Figure 4:
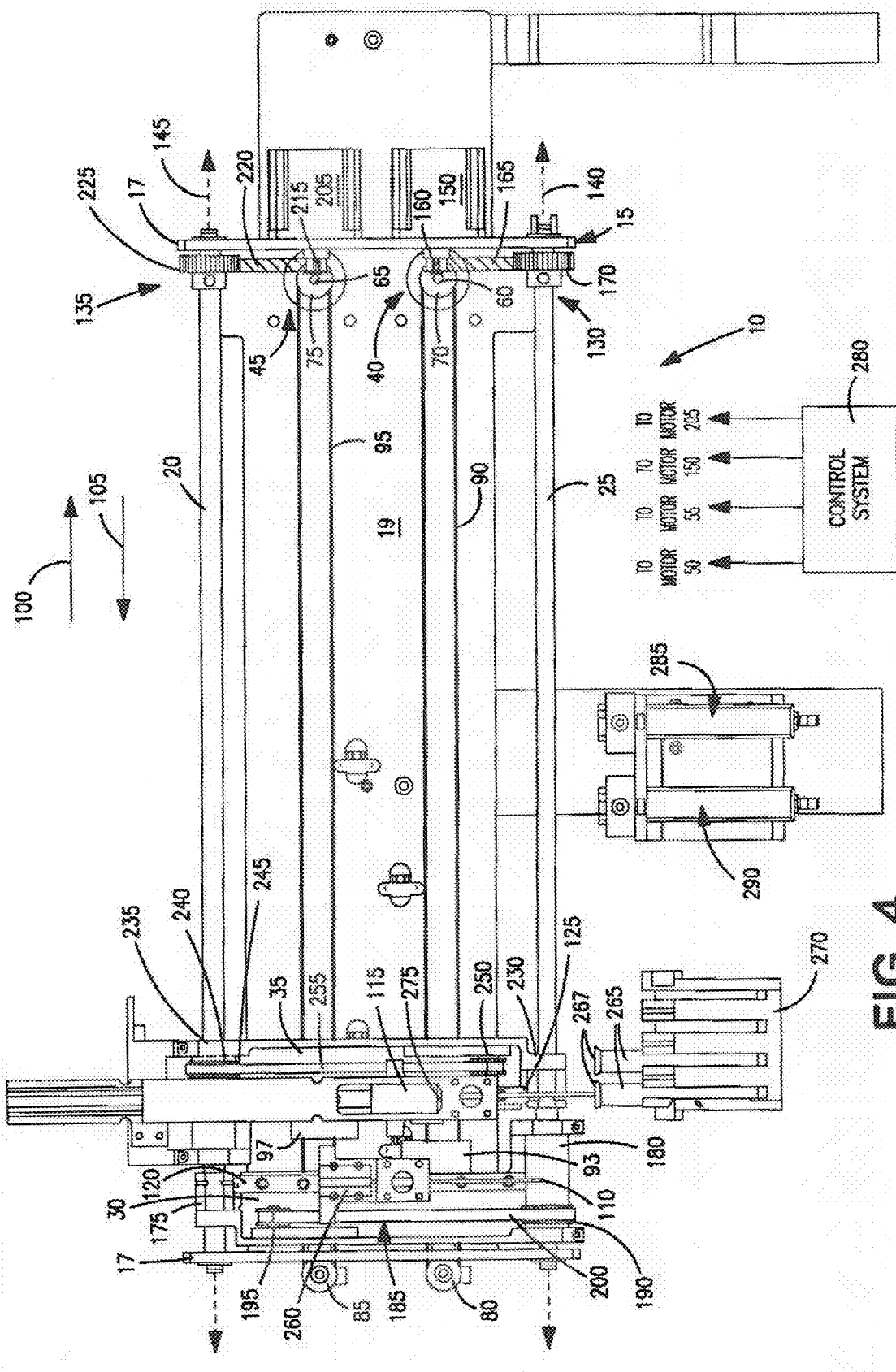
FIG. 4 is a front view of the gantry assembly in the state illustrated in FIG. 3.

A first embodiment of an improved gantry assembly suitable for use in a laboratory apparatus is shown generally at 10 of FIGS. 1 through 4. The gantry assembly 10 includes a frame 15 having a pair of upstanding side plates 17 that are connected by a backplate 19. Side plates 17 of the frame 15 support an upper horizontally oriented guide rod 20 and a lower horizontally oriented guide rod 25. A plurality of carriage assemblies are connected for horizontal movement along the plurality of guide rods 20 and 25. In the illustrated embodiment, two carriage assemblies 30 and 35 are employed. Each carriage assembly 30 and 35 is independently movable along guide rods 20 and 25 by respective carriage drive assemblies 40 and 45.

In the illustrated embodiment, each carriage drive assembly 40 and 45 includes a respective motor 50 and 55 having a corresponding rotor shaft 60 and 65. Rotor shafts 60 and 65 extend through backplate 19 to engage drive wheels 70 and 75. Each drive wheel 70 and 75 is respectively associated with a corresponding idler wheel 80 and 85 that is in fixed engagement with the backplate 19 of frame 15. Elastic drive belts 90 and 95 are connected for rotation about and extend between the respective drive wheels 70 and 75 and idler wheels 80 and 85.

Carriage assembly 30 is fixed for co-movement with elastic drive belt 90 while carriage assembly 35 is fixed for co-movement with elastic drive belt 95. To this end, the rear portion of carriage assembly 30 is fixed with either the upper or lower length of drive belt 90 by a corresponding drive clamp 93. Similarly, the rear portion of carriage assembly 35 is fixed with either the upper or lower length of drive belt 95 by drive clamp 97. For descriptive purposes, it is assumed that each carriage assembly 30 and 35 is fixed for movement with the upper length of the corresponding drive belt 90 and 95. As such, rotation of the rotor shafts 60 and 65 of motors 50 and 55 in a clockwise direction will result in linear movement of the corresponding carriage assembly 30 and 35 in the direction of arrow 100 along guide rods 20 and 25. Similarly, rotation of the rotor shafts 60 and 65 of motors 50 and 55 in a counterclockwise direction will result in linear movement of the corresponding carriage assembly 30 and 35 in the direction of arrow 105 along guide rods 20 and 25. Whether carriage assemblies 30 and 35 are connected to the upper or lower lengths of their respective elastic drive belts 90 and 95 is dependent on design requirements.

At least one of the carriage assemblies 30 and 35 includes a corresponding sub-carriage assembly that can be moved in a direction transverse to the guide rods 20 and 25. In the illustrated embodiment, two sub-carriage assemblies 110 and 115 are employed. Sub-carriage assembly 110 is carried by and engages carriage assembly 30 at a vertically oriented track 120 disposed at a front side of the assembly 30. Similarly, sub-carriage assembly 115 is carried by and engages carriage assembly 35 at a vertically oriented track 125 disposed at a front side of the assembly 35. In each instance, sub-carriage assemblies 110 and 115 can be moved vertically along the corresponding tracks 120 and 125.

Movement of each sub-carriage assembly 110 and 115 is facilitated by respective sub-carriage drive mechanisms, shown generally at 130 and 135. In the illustrated embodiment, carriage assembly 30 is connected to guide rod 25 so that sub-carriage assembly 110 is driven vertically when guide rod 25 is rotated about axis 140. Preferably, the connection between carriage assembly 35 and guide rod 25 does not generate a corresponding vertical movement of sub-carriage assembly 115. Rather, carriage assembly 35 is connected to guide rod 20 so that sub-carriage assembly 115 is driven vertically when guide rod 20 is rotated about axis 145. In this manner, each sub-carriage assembly 110 and 115 can be moved vertically independent of one another by rotation of the corresponding guide rod 20 and 25.

In the illustrated embodiment, sub-carriage drive mechanism 130 includes a drive motor 150 having a rotor shaft 155 extending through side plate 17 of frame 15 to engage a drive wheel 160. Rotational movement of drive wheel 160 is transferred through an elastic drive belt 165 to a gear wheel 170 that is fixed to guide rod 25. Carriage assembly 30 engages guide rod 20 at a restraining bushing 175 and engages guide rod 25 at a keyed connection 180 of a translational drive 185. Keyed connection 180 preferably comprises a spline nut that engages a spline in guide rod 25. Translational drive 185 includes a drive wheel 190 that is connected for co-rotation with guide rod 25, an idler wheel 195 and an elastic drive belt 200 connected for rotation about and extending between the drive wheel 190 and idler wheel 195. Sub-carriage assembly 110 is fixed to either the front or rear length of elastic drive belt 200. As such, rotation of the elastic drive belt 200 about the drive wheel 190 and idler wheel 195 results in a corresponding linear movement of the sub-carriage assembly 110 along the track 120 in a direction transverse to the guide rods 20 and 25.

Sub-carriage drive mechanism 135 includes a drive motor 205 having a rotor shaft 210 extending through side plate 17 of frame 15 to engage a drive wheel 215. Rotational movement of drive wheel 205 is transferred through an elastic drive belt 220 to a gear wheel 225 that is fixed to guide rod 20. Carriage assembly 35 engages guide rod 25 at a bushing 230 and engages guide rod 20 at a keyed connection 235 of a translational drive 240. Keyed connection 235 preferably comprises a spline nut that engages a spline in guide rod 20. Translational drive 240 includes a drive wheel 245 that is connected for co-rotation with guide rod 20, an idler wheel 250 and an elastic drive belt 255 connected for rotation about and extending between the drive wheel 245 and idler wheel 250. Sub-carriage assembly 115 is fixed to either the front or rear length of elastic drive belt 255. As such, rotation of the elastic drive belt 255 about the drive wheel 245 and idler wheel 250 results in a corresponding linear movement of the sub-carriage assembly 115 along track 125 in a direction transverse to the guide rods 20 and 25. Whether sub-carriage assemblies 110 and 115 are fixed to the front or rear length of their corresponding elastic drive belts 200 and 255 depends on design requirements that can be readily ascertained during the system specification process.

Sub-carriage assemblies 110 and 115 each carry tools that are used to manipulate chemical and/or biological materials disposed in a container. For example, sub-carriage assemblies 110 and 115 may each carry a sample preparation tool such as a homogenizer, a blender blade, a pipette probe, a mixer, and at a rater, a fluid dispenser, a hollow fiber filtration cartridge, a drive reagent transferred device, etc. In the embodiment shown in FIGS. 1 through 4, sub-carriage assembly 115 includes a blade tool 260 that is adapted to pierce the sealed caps of, for example, containers 265 (i.e., sealed test tubes) supported on a rack 270. Sub-carriage assembly 110, in turn, includes a sampling tool 275 that is adapted to enter container 265 through an opening formed by blade 260 and aspirate an amount of material content therefrom.

Drive motors 50, 55, 150 and 205 are connected to a control system 280. Control system 280 is preferably programmable and is adapted to direct carriage drive mechanisms 40 and 45 to move the first and second carriage assemblies 30 and 35 to operable positions with respect to containers 265 in accordance with a predetermined operational sequence. Control system 280 is further adapted to direct sub-carriage drive mechanisms 130 and 135 to move sub-carriage assemblies 110 and 115 vertically for engagement with and extraction from containers 265 in accordance with the predetermined operational sequence. One example of such an operational sequence includes the following steps:

- moving carriage assembly 30 horizontally along guide rods 20 and 25 so that the blade tool 260 on sub-carriage assembly 110 is juxtaposed the sealed cap 267 of a container 265;
- lowering the sub-carriage assembly 110 of carriage assembly 30 vertically downward along track 120 by rotating guide rod 25 so that the blade tool 260 pierces the cap 267 to form an opening therein (see FIGS. 1 and 2);
- raising the sub-carriage assembly 110 of carriage assembly 30 vertically along track 120 by rotating guide rod 25 so that the blade tool 260 disengages from the cap 267;
- moving carriage assembly 30 horizontally along guide rods 20 and 25 to remove the carriage assembly 30 and corresponding blade tool 260 from alignment with the container 265;
- moving carriage assembly 35 horizontally along guide rods 20 and 25 so that the sampling tool 275 is juxtaposed the opening in the cap 267 of the container 265;
- lowering sub-carriage assembly 115 vertically along track 125 by rotating guide rod 20 so that the sampling tool 275 proceeds through the opening in the cap 267 and into contact with the material held in the container 265 (see FIGS. 3 and 4);
- activating the sampling tool 275 to extract an amount of material from the container 265; and
- raising sub-carriage assembly 115 vertically along track 125 by rotating guide rod 20 so that the sampling tool 275 disengages from the opening in the cap 267.

Once an amount of material is present in sampling tool 275, carriage assembly 35 may be moved into juxtaposition with a slide maker, another container, etc., for dispensing of the material therefrom for further manipulation, analysis and/or processing.

Before the next material sampling sequence is initiated, the sampling tool 275 and blade tool 260 should be washed to prepare them for further use. To this end, assembly 10 may include one or more cleaning apparatus to wash the tools carried by the sub-carriage assemblies 110 and 115. In the particular embodiment illustrated in FIGS. 1 through 4, assembly 10 includes a blade washer 285 and a sampling tool washer 290. Each washer 285 and 290 includes features that are unique to washing the particular sub-carriage tool with which it is associated. It will be evident, however, that a single washer may be used in those instances in which the washing requirements for the sub-carriage tools are the same. Alternatively, a single washer may be used to implement different washing protocols for different sub-carriage tools. In each instance, the carriage assemblies 30 and 35 are driven horizontally along guide rods 20 and 25, concurrently or at different times, so that the tools carried by the corresponding sub-carriage assemblies 110 and 115 are juxtaposed the respective washer. The corresponding guide rod 20 or 25 is then rotated to drive the tool carried by the sub-carriage assembly 110 and 115 into engagement with the corresponding washer 285, 290.

Figure 5:
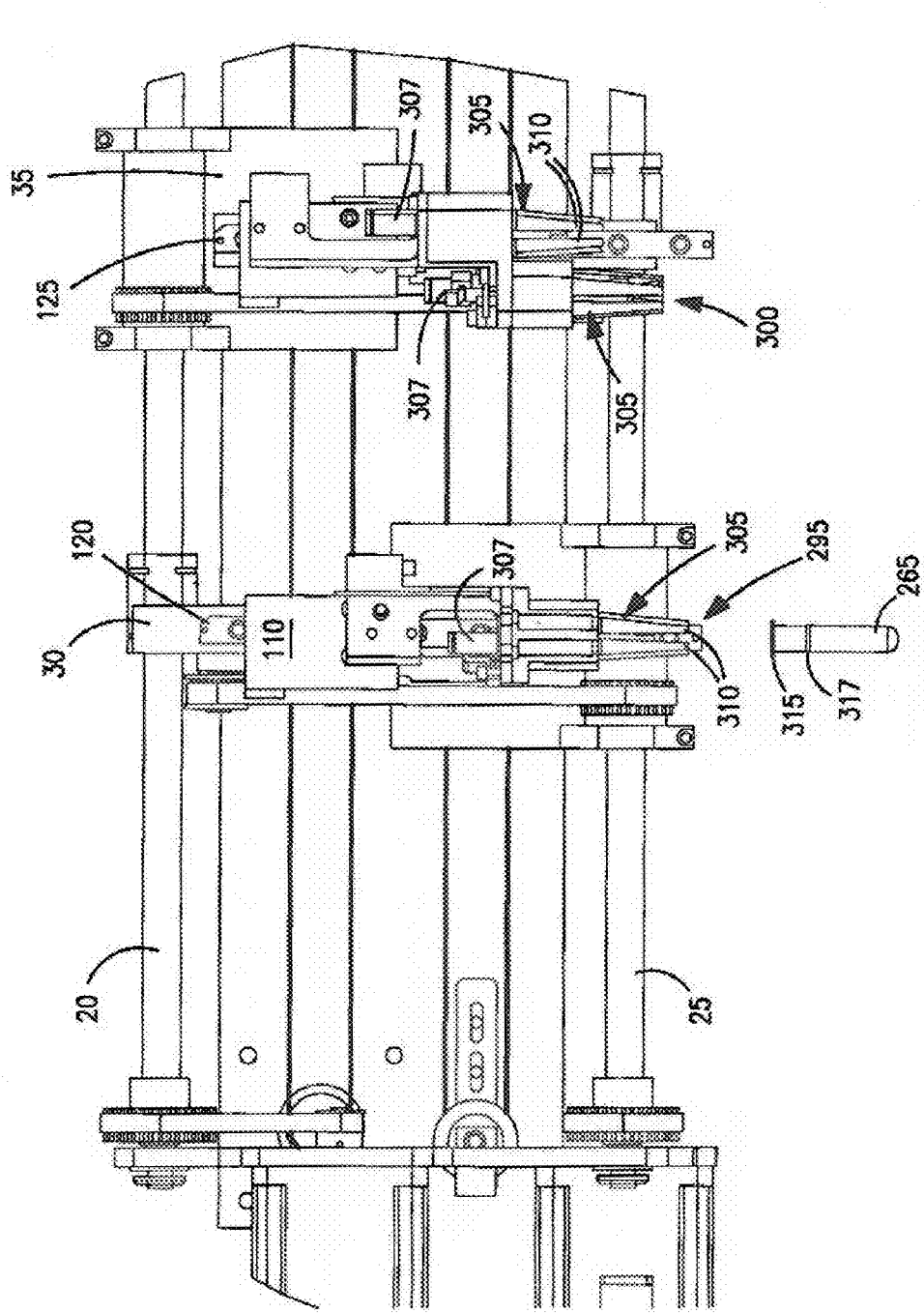
FIG. 5-7 are front views of a further embodiment of a gantry assembly constructed in accordance with the teachings of the present invention in which the sub-carriage assemblies include heads that are adapted to engage, manipulated and transport containers.
Figure 6:
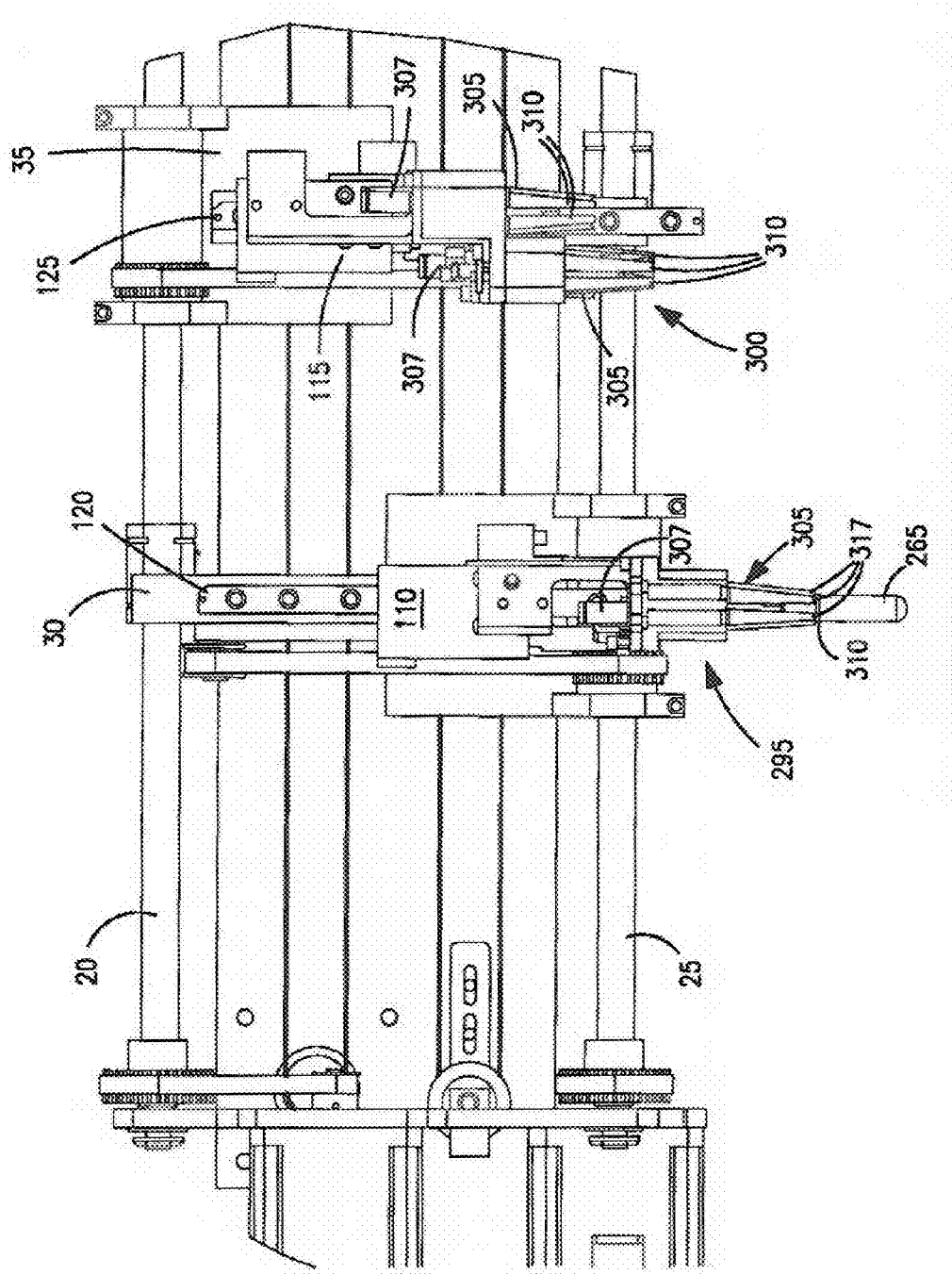
Figure 7:
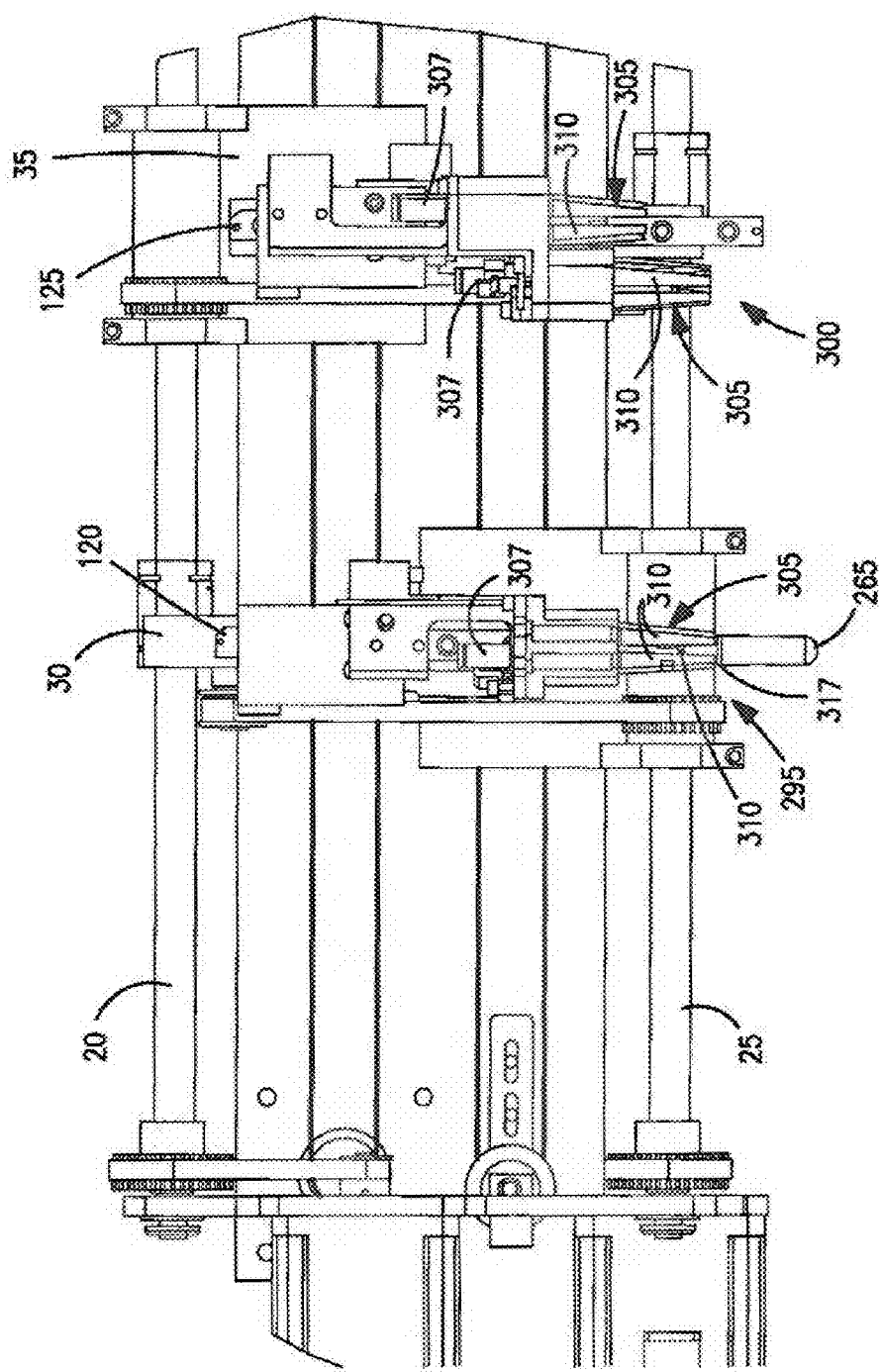

FIGS. 5 through 7 illustrate an embodiment of assembly 10 in which the tools on the sub-carriage assemblies 110 and 115 are adapted to engage, lift and transport containers 265. In the specific embodiment shown here, sub-carriage assembly 110 carries a single head assembly 295 that is adapted to engage a single container 265 while sub-carriage assembly 115 carries a multiple head assembly 300 that is adapted to engage multiple containers 265.

The heads 305 on both the single and multiple head assemblies 295 and 300 can be constructed in a variety of different manners. For example, each head 305 may include a plurality of downwardly extending resilient arms 310 disposed in an inverted frustoconical arrangement. As shown in FIG. 6, single head assembly 295 has been driven into engagement with a corresponding container 265 by first driving carriage assembly 30 to place the sub-carriage assembly 110 into a position juxtaposed container 265. Sub-carriage assembly 110 carrying single head assembly 295 is then driven downward so that the resilient arms 310 bend outward about a rib 315 at the exterior of container 265. With the resilient arms 310 engaging rib 315, sub-carriage assembly 110 may be raised to lift container 265 while carriage assembly 30 may be moved horizontally to place the container 265 at the desired horizontal position. A further rib 317 assists in restricting the vertical movement of the container 265 while it is supported in head 305. Raising of the container 265 by sub-carriage assembly 110 is shown in FIG. 7.

Removal of the container 265 from a head 305 can likewise be accomplished in a variety of different manners. For example, a piston drive or the like 307 that is disposed in the head 305 may be driven downward into engagement with container 265 to dislodge the container 265 from its frictional grip between arms 310. Alternatively, or in addition, such a piston drive 307 may be configured to separate resilient arms 310 to thereby release container 265. Still further, a removal mechanism that is completely separate from the gantry assembly 10 may be used to grasp a lower portion of the container 265 and pull it from the resilient arms 310 once the container 265 reaches the desired position.

In a still further embodiment, the arms 310 of heads 305 may be constructed as rigid members. In such instances, the drive 307 is connected to separate the arms 310 as the container 265 is introduced therebetween and closes the arms 310 once the container 265 is positioned to be gripped.

As noted above, multiple head assembly 295 includes a plurality of heads 305. In the illustrated embodiment, the heads 305 of multiple head assembly 295 are connected for concurrent vertical movement along track 125. However, it will be recognized that heads 305 may be disposed on opposite sides of track 125 and connected to opposite lengths of elastic drive belt 255. Driving heads 305 in this manner results in reciprocal movement of the heads 305 in that one head 305 will be raised as the other head 305 is lowered.

A number of advantages flow from the specific embodiments of the gantry assembly 10 described above. For example, movement of the carriage assemblies 30 and 35 in horizontal directions is stabilized by both guide rods 20 and 25 while vertical movement of the sub-carriage assemblies 110 and 115 is facilitated by a respective one of the guide rods 20 and 25. As a result, the gantry assembly design is mechanically stable yet efficient in its use of space and components. One way that this may be achieved is through the use of single hardware components having multiple functions.

Further, the independent operation of carriage assemblies 30 and 35 and sub-carriage assemblies 110 and 115 facilitates use of the gantry assembly 10 in a wide range of material handling protocols. For example, prior single carriage gantry assembly designs necessarily required that the containers 265 be presented in a linear and sequential manner to the gantry assembly in a direction perpendicular to the horizontal motion of the carriage if spacing between the containers 265 was to be optimal. In the improved gantry designs set forth above, the multiple independently operable carriage assemblies and sub-carriage assemblies allow the apparatus designer to vary the manner in which containers 265 are to be presented to the gantry assembly. For example, the containers 265 can be presented along an axis that is parallel to the horizontal motion path of the carriage assemblies 30 and 35 (see FIGS. 1 through 4). Unlike single carriage apparatus, the spacing between the containers 265 is no longer strictly limited when the containers are presented in this orientation.

The independent operation of the carriage assemblies 30 and 35 and sub-carriage assemblies 110 and 115 further facilitates increased throughput compared to prior single carriage designs since each carriage assembly/sub-carriage assembly can attend to a specific step in the overall processing protocol independent of the motion and operation of the other. As such, complex processing protocols can be executed in short periods of time.

Numerous modifications may be made to the foregoing system without departing from the basic teachings thereof. Although the present invention has been described in substantial detail with reference to one or more specific embodiments, those of skill in the art will recognize that changes may be made thereto without departing from the scope and spirit of the invention as set forth in the appended claims.

What is claimed is:

1. A laboratory instrument adapted to extract an amount of material from a container for testing thereof, said laboratory instrument comprising:
   a rack adapted to support a container;
   a first carriage assembly having a piercing tool adapted to pierce a sealed cap of a container supported by said rack;
   a second carriage assembly having a sampling tool adapted to enter said container supported by said rack through an opening formed by said piercing tool, said sampling tool further being adapted to extract said amount of said material from said container, said first and second carriage assemblies being mounted on a common gantry;
   a plurality of drive mechanisms adapted to independently move said first and second carriage assemblies into various operable positions with respect to said container; and
   a control system adapted to direct said plurality of drive mechanisms to move said first and second carriage assemblies to said operable positions in accordance with a predetermined operational sequence, wherein said predetermined operational sequence comprises:
   moving said first carriage assembly along a first motion path so that said piercing tool is juxtaposed a sealed cap of a container supported by said rack;
   moving said first carriage assembly along a second motion path so that said piercing tool engages said sealed cap to form an opening therein;
   moving said first carriage assembly along said second motion path so that said piercing tool disengages from said sealed cap; and
   moving said first carriage assembly along said first motion path to remove said piercing tool from alignment with said container.

2. A laboratory instrument as claimed in claim 1 wherein said predetermined operational sequence further comprises:
   moving said second carriage assembly along a third motion path so that said sampling tool is juxtaposed said opening in said sealed cap of said container;
   moving said second carriage assembly along a fourth motion path so that said sampling tool proceeds through said opening in said sealed cap and into contact with a sample material held in said container;
   activating said sampling tool to extract an amount of said sample material from said container; and moving said second carriage assembly along said fourth motion path so that said sampling tool disengages said opening in said sealed cap.

3. A laboratory instrument as claimed in claim 2 wherein said first and third motion paths lie generally along the same motion axis.

4. A laboratory instrument as claimed in claim 3 wherein said second and fourth motion paths lie generally along the same motion axis.

5. A laboratory instrument as claimed in claim 2 wherein said second and fourth motion paths lie generally along the same motion axis.

6. A laboratory instrument as claimed in claim 5 wherein said first and third motion paths are generally transverse to said second and fourth motion paths.

7. A laboratory instrument as claimed in claim 2 wherein said predetermined operational sequence further comprises:
   moving said second carriage assembly along a fifth motion path so that said sampling tool is placed in a position juxtaposed a test container;
   moving said second carriage assembly along a sixth motion path so that said sampling tool is disposed in said test container;
   activating said sampling tool to dispense the material extracted from said container into said test container; and
   moving said second carriage assembly along said sixth motion path so that said sampling tool is removed from engagement with said test container.

8. A laboratory instrument as claimed in claim 7 wherein said predetermined operational sequence further comprises:
   moving said second carriage assembly along a seventh motion path so that said sampling tool is juxtaposed a cleaning apparatus; and
   moving said second carriage assembly along an eighth motion path so that said sampling tool is placed into engagement with said cleaning apparatus.

9. A laboratory instrument as claimed in claim 1 wherein the common gantry includes a first guide rod and a second guide rod disposed generally parallel with one another; and
   wherein the first and second carriage assemblies are connected for movement along the first and second guide rods and wherein the first carriage assembly includes a first keyed connection engaged to the first guide rod and a first non-keyed bushing engaged to the second guide rod and wherein the second carriage assembly includes a second keyed connection engaged to the second guide rod and a second non-keyed bushing engaged to the first guide rod.

10. A laboratory instrument as claimed in claim 9 wherein the piercing tool moves in response to rotation of the first guide rod, and the sampling tool moves in response to rotation of the second guide rod.

11. A laboratory instrument as claimed in claim 1 wherein the plurality of drive mechanisms adapted to independently move said first and second carriage assemblies into various operable positions includes a first motor having a rotating shaft;
- a first drive wheel connected for rotation by the rotating shaft of the first motor;
- a first idler wheel; and
- a first elastic drive belt connected for rotation about and extending between the first drive wheel and the first idler wheel, the first carriage being connected for co-movement with the first elastic drive belt.

12. A laboratory instrument as claimed in claim 11 wherein the plurality of drive mechanisms adapted to independently move said first and second carriage assemblies into various operable positions further includes a second motor having a rotating shaft;
- a second drive wheel connected for rotation by the rotating shaft of the second motor;
- a second idler wheel; and
- a second elastic drive belt connected for rotation about and extending between the second drive wheel and the second idler wheel, the second carriage being connected for co-movement with the second elastic drive belt.

13. In a laboratory instrument having a rack adapted to support a container, a first carriage assembly having a piercing tool adapted to pierce a sealed cap of a container supported by said rack and a second carriage assembly having a sampling tool adapted to enter said container supported by said rack through an opening formed by said piercing tool and wherein said first and second carriage assemblies are mounted on a common gantry, a method for extracting an amount of material from said container comprising:
- moving said first carriage assembly along a first motion axis so that said piercing tool is juxtaposed a sealed cap of a container supported by said rack;
- moving said first carriage assembly along a second motion axis so that said piercing tool engages said sealed cap to form an opening therein;
- moving said first carriage assembly along said second motion axis so that said piercing tool disengages from said sealed cap;
- moving said first carriage assembly along said first motion axis to remove said piercing tool from alignment with said container;
- moving said second carriage assembly along said first motion axis so that said sampling tool is juxtaposed said opening in said sealed cap of said container;
- moving said second carriage assembly along said second motion axis so that said sampling tool proceeds through said opening in said sealed cap and into contact with a sample material held in said container;
- activating said sampling tool to extract an amount of said sample material from said container; and moving said second carriage assembly along said second motion axis so that said sampling tool disengages said opening in said sealed cap.

14. The method as claimed in claim 13 and further comprising:
- moving said second carriage assembly along said first motion axis so that said sampling tool is placed in a position juxtaposed a test container;
- moving said second carriage assembly along said second motion axis that said sampling tool is disposed in said test container;
- activating said sampling tool to dispense the material extracted from said container into said test container;
- moving said second carriage assembly along said second motion axis so that said sampling tool is removed from engagement with said test container.

15. A method as claimed in claim 14 and further comprising:
- moving said second carriage assembly along said first motion axis so that said sampling tool is juxtaposed a cleaning apparatus; and
- moving said second carriage assembly along said second motion axis so that said sampling tool is placed into engagement with said cleaning apparatus.

16. The method as claimed in claim 13 wherein the first motion axis includes a first guide rod and a second guide rod and wherein the step of moving the first carriage assembly along the second motion axis includes rotating the first guide rod.

17. The method as claimed in claim 16 wherein the step of moving the second carriage assembly along the second motion axis includes rotating the second guide rod.

18. The method as claimed in claim 16 wherein the first carriage assembly includes a first keyed connection engaged to the first guide rod and a first non-keyed bushing engaged to the second guide rod.

19. The method as claimed in claim 16 wherein the second carriage assembly includes a second keyed connection engaged to the second guide rod and a second non-keyed bushing engaged to the first guide rod.

* * * * *

UNITED STATES PATENT AND TRADEMARK OFFICE
CERTIFICATE OF CORRECTION

PATENT NO. : 7,662,339 B2  Page 1 of 1
APPLICATION NO. : 10/972164
DATED : February 16, 2010
INVENTOR(S) : Mattila et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1423 days.

Signed and Sealed this

Thirtieth Day of November, 2010

David J. Kappos
*Director of the United States Patent and Trademark Office*